Figure 1:
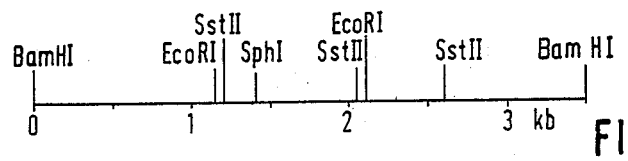

United States Patent [19]

Muth et al.

[11] Patent Number: 4,965,207

[45] Date of Patent: Oct. 23, 1990

[54] **COLOR MARKER FOR CLONINGS IN *STREPTOMYCES LIVIDANS***

[75] Inventors: Günter Muth; Wolfgang Wohlleben; Alfred Pühler, all of Bielefeld; Gerhard Wöhner, Flörsheim am Main; Rüdiger Marquardt, Frankfurt am Main, all of Fed. Rep. of Germany

[73] Assignee: Hoechst Aktiengesellschaft, Frankfurt am Main, Fed. Rep. of Germany

[21] Appl. No.: 83,805

[22] Filed: Aug. 11, 1987

[30] Foreign Application Priority Data

Aug. 13, 1986 [DE] Fed. Rep. of Germany ....... 3627392

[51] Int. Cl.$^5$ .................. C12N 15/00; C12N 1/20; C12N 1/00; C12P 21/00; C07H 21/04
[52] U.S. Cl. .................... 435/320; 435/69.1; 435/71.2; 435/71.3; 435/252.35; 435/886; 530/27; 935/11; 935/29
[58] Field of Search ............. 435/68, 91, 172.1, 172.3, 435/320, 252.3, 252.31–252.35, 886, 69.1, 71.1, 71.3, 71.2; 536/27; 935/11, 14, 29, 75

[56] References Cited

U.S. PATENT DOCUMENTS 4,828,998  5/1989  Wohner et al. ................... 435/886

FOREIGN PATENT DOCUMENTS 0154430  11/1985  European Pat. Off. ......... 435/172.3

OTHER PUBLICATIONS

Feitelson et al.; J. Gen. Microbiol. 131: 2431 (1985).
Horinouchi et al.; J. Bacteriol. 155: 1238 (1983).
Piruzyan, et al., "Cloning of DNA Fragments of *Streptomyces coelicolor* A3(2) Plasmid . . . ", Chemical Abstracts, vol. 98, No. 7, 47927w (1983).
Horinouchi, et al., "Construction and Application of a Promoter–Probe Plasmid . . . ", Journal of Bacteriology, vol. 162, No. 1:406–412 (1985).
Chater, et al., "Gene Cloning in Streptomyces", Curr. Top. Microbiol. Immunol., vol. 96:69–95 (1982).
Feitelson, et al., "Molecular Genetics of Red Biosynthesis in Streptomyces", Journal of Natural Products, vol. 49, No. 6:988–994 (1986).
Katz, E., et al., "Cloning and Expression of the Tyrosinase Gene from *Streptomyces antiboiticus* in *Streptomyces lividans*", J. Gen'l Microbiology 129:2703–14 (1983).

Primary Examiner—James Martinell
Attorney, Agent, or Firm—Finnegan, Henderson, Farabow, Garrett, and Dunner

[57] ABSTRACT

Intensely crimson colonies are obtained from *Streptomyces coelicolor* DSM 3030 by total digestion of the total DNA, cloning into a suitable vector, and transformation of *Streptomyces lividans*. Re-isolation of the plasmid DNA and cutting with BamHI results in fragments about 3.4 to 9 kb in length, on which is located the gene which determines production of the coloring agent. This gene is suitable as marker, in particular as inactivation marker, in Streptomycetes.

6 Claims, 1 Drawing Sheet

COLOR MARKER FOR CLONINGS IN *STREPTOMYCES LIVIDANS*

The mel gene is presently known as color marker for cloning into Streptomycetes (E. Katz et al., J. Gen. Microbiol. 129 (1983) 2703) since it codes for tyrosinase and thus via-intermediates-is responsible for producing the coloring agent melanin. This gene is contained by, for example, the commercially available plasmid pIJ702, which can be obtained from the John Innes Foundation, Norwich, England, and is described, for example in D. A. Hopwood et al., Genetic Manipulation of Streptomyces-A Laboratory Manual, The John Innes Foundation, 1985, pages 292 et seq.

DNA fragments which are expressed in *Streptomyces lividans* and bring about in the medium an intense crimson coloration which shows little diffusion in solid media have now been found.

Hence the invention relates to DNA fragments which bring about the expression of a red coloring agent in *Streptomyces lividans*. These can be obtained from the total DNA of *Streptomyces coelicolor* DSM 3030 by cutting with BamHI, cloning of the fragments into a suitable vector, and selection for production of red coloring agent. The starting strain *S. coelicolor* DSM 3030 is mentioned in the European Patent Application with the publication number 0 181 562 as producer of a bacteria-lysing enzyme.

G. Habermehl et al., Z. Naturforsch. 32b (1977) 1195, describe the isolation, fractionation and structure-elucidation of the blue bacterial pigment "amylocyanin" from *Streptomyces coelicolor* Müller, DSM 40665. In addition to this water-soluble blue coloring agent, in the late phase of growth additional pigments, including red substances, are also produced but have not been identified in detail.

The invention furthermore relates to the use of the DNA fragments according to the invention as markers, in particular as inactivation markers, in Streptomycetes plasmids.

Further aspects of the invention, and its preferred embodiments, are evident from the description which follows and from the patent claims.

To isolate the DNA fragments, the total DNA from the strain *Streptomyces coelicolor* DSM 3030 is isolated by cutting with the restriction enzyme BamHI and shotgun cloning into a suitable vector, transformation of a Streptomycetes recipient strain and selection for production of coloring agent. The positive clones contain various DNA fragments of about 3.4 to 9 kb from DSM 3030. FIG. 1 shows a restriction map of the 3.4 kb fragments.

The red coloring agent which is formed is readily soluble in water. The crimson color of the colonies results from a high concentration of coloring agent. In a solid medium the fraction of coloring agent which remains bound to mycelium predominates, and only a small fraction diffuses into the medium. The appearance under the microscope is characteristic: the coloring agent is located in tightly packed spherical bodies on the mycelium and thus makes the colony appear intensely crimson. In liquid culture (tryptic soya broth, "lysis medium A", European Patent Application with the publication number 0 158 872, page 6) a culture supernatant which is intensely red in color is obtained after about 3 days. In solid media too, production of the coloring agent takes place irrespective of the medium used ("R2YE" (Hopwood et al., loc. cit.), sporulation medium (German Offenlegungsschrift 3 331 860, Example 1, third medium), "Penassay", "Penassay" with added antibiotics).

The red coloring agent is formed even at the start of growth of the colony and is thus obviously not a product of secondary metabolism. In contrast to this, the wild type of *S. lividans* does not produce a red pigment until near the end of vegetative growth (Horinouchi et al., Agric. Biol. Chem. 48 (1984) 2131).

The 3.4 kb fragment shown in FIG. 1 has a number of cleavage sites which are suitable for subcloning experiments. It contains no cleavage sites for the enzymes XhoI, HindIII and PstI.

The red phenotype of plasmid-containing host cells is plasmid-coded, as can be shown by plasmid isolation and retransformation.

The DNA fragments according to the invention code either directly for production of the red coloring agent or for a regulation gene which induces this production in *S. lividans*. The presence of a regulation gene is indicated by the fact that no such production of coloring agent takes place in *S. prasinus* and *S. ghanaensis*. Thus the DNA fragments according to the invention are suitable not only generally for cloning experiments but also specifically for tracing metabolic pathways in Streptomycetes. This is indicated by the results of Horinouchi et al., loc. cit. and J. Bacteriol. 158 (1984), 481-487, who have shown that it is possible to clone from *S. bikiniensis* a regulator gene which stimulates the production of red pigments in *S. lividans*.

The invention is illustrated in detail in the examples which follow. Unless otherwise specified, in these examples percentage data and parts relate to weight.

The figures are true to scale, with the exception of the polylinker regions.

Example 1: Preparation of the vector pGM4

Figure 2:
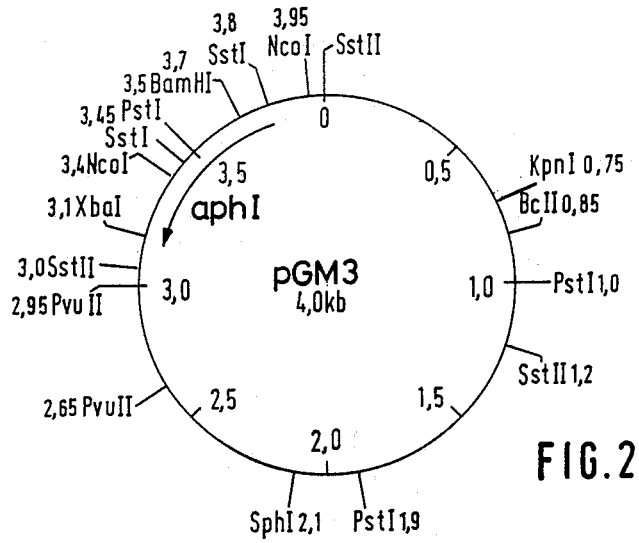

The plasmid pGM1 (European Patent Application with the publication number 0 158 872, FIG. 2) is partially digested with SstII to allow a 3.0 kb fragment to be obtained. The plasmid pSLE16 (European Patent Application with the publication number 0 158 201, FIG. 18) is cut with SstII to allow the 1 kb fragment which contains the neomycin resistance gene aphI to be obtained. Ligation of the two fragments results in the plasmid pGM3 (FIG. 2).

Figure 3:
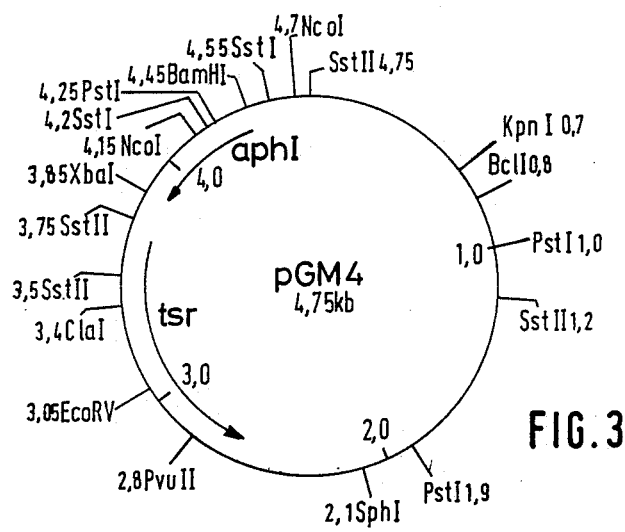

In addition, pSLE41 (European Patent Application A2 0 158 201, FIG. 20) is cut with BclI to allow isolation of a 1 kb fragment, whose protruding ends are filled in with Klenow polymerase. pGM3 is now cut with PvuII, and the 0.3 kb fragment is deleted. The remaining plasmid is now ligated with the BclI fragment which has been made bluntended, resulting in the plasmid pGM4 (FIG. 3).

Example 2: Preparation of a gene bank

*S. coelicolor* DSM 3030 is lysed, and the DNA is isolated in a known manner. The latter is totally digested with BamHI. The plasmid pGM4 (FIG. 3) is cut with BamHI, treated with alkaline phosphatase and ligated with the BamHI fragments. The plasmid population obtained in this way is tranformed into the recipient strain *S. lividans* TK 23 (Obtainable from the John Innes Foundation). When 1 μg of ligation mixture is used, about 20000 thiostrep-tone-resistant transformants are obtained, of which 80% are sensitive to neomycin and consequently contain an insert.

Example 3: Isolation of the DNA fragments according to the invention

Among 500 transformants, on average one colony with an intense crimson color was found. This was separated off, and the plasmid DNA from these clones was isolated. Subsequent re-transformation into *S. lividans* TK 23 resulted in colonies which were exclusively red.

Characterization of the plasmid DNA showed that 3.4 to 9 kb BamHI fragments had been inserted into the aphI gene of pGM4. The plasmid with the 3.4 kb insert was called pGM97.

Example 4: Transformation

The plasmid pGM97 was transformed into various commercially available strains of *S. lividans*. All showed expression of the red coloring agent, both in liquid and in solid media.

DSM 3030 has been deposited at the Deutsche Sammlung von Mikrooganismen und Zellculturen, Mascheroder Weg 1b, D-3300 Braunschweig, West Germany.

We claim:

1. DNA fragments which effect the expression of a red coloring agent in *Streptomyces lividans*, which DNA fragments are obtainable from the total DNA of *Streptomyces coelicolor* DSM 3030 by cutting said total DNA with BamHI, cloning of the DNA fragments into a vector, transforming *S. lividans*, and selecting for production of a red coloring agent.

2. The DNA as claimed in claim 1, having restriction sites as set forth in the restriction map of FIG. 1.

3. A plasmid which is capable of amplifying in a Streptomyces strain, containing as a marker the DNA fragment claimed in claim 1.

4. A plasmid which is capable of amplifying in a Streptomyces strain, containing as a marker the DNA fragment claimed in claim 2.

5. A plasmid as claimed in claim 3, wherein the marker serves as an inactivation marker.

6. A plasmid as claimed in claim 4, wherein the marker serves as an inactivation marker.

* * * * *